United States Patent [19]
Ostlund et al.

[11] Patent Number: 5,827,896
[45] Date of Patent: *Oct. 27, 1998

[54] PINITOL AND DERIVATIVES THEREOF FOR THE TREATMENT OF METABOLIC DISORDERS

[75] Inventors: Richard E. Ostlund, Ladue; William R. Sherman, University City, both of Mo.

[73] Assignee: Washington University, St. Louis, Mo.

[ * ] Notice: The term of this patent shall not extend beyond the expiration date of Pat. No. 5,550,166.

[21] Appl. No.: 610,039

[22] Filed: Mar. 4, 1996

Related U.S. Application Data

[63] Continuation-in-part of Ser. No. 407,430, Mar. 17, 1995, Pat. No. 5,550,166.

[51] Int. Cl.⁶ .................................................. A61K 31/075
[52] U.S. Cl. .............................................................. 514/715
[58] Field of Search ............................................. 514/715

[56] References Cited

U.S. PATENT DOCUMENTS 5,550,166  8/1996  Ostlund et al. .

OTHER PUBLICATIONS

"Hypoglycaemic Plants—A Review", Handa, S.S., et al., Fitoterapia, vol. 60, No. 3, (1989), pp. 195–224.

"Pinitol–A New Anti–Diabetic Compound From the Leaves of *Bougainvillea Spectabilis*", Narayanan, et al., Current Science, vol. 56, No. 3, (1987), pp. 139–141.

"Preferential Leaching of Pinitol from Soybeans During Imbibition", Philip Nordin, Plant Physiol., vol. 76, No. 2, (1984), pp. 313–315.

"Cyclitols in Soybean", Phillips, et al., Agric. Food Chem., vol. 30, No. 1, (1982).

*Primary Examiner*—Kimberly Jordan
*Attorney, Agent, or Firm*—Craig M. Bell; Dann, Dorfman, Herrell and Skillman

[57] ABSTRACT

Pinitol and derivatives and metabolites thereof are useful in nutritional and medicinal compositions for lowering plasma free fatty acid levels and for treating conditions associated with insulin resistance, such as diabetes mellitus and its chronic complications; obesity; hyperlipidemias and dyslipidemias atherosclerosis; hypertension; cardiovascular disease; AIDS; cancer; wasting/cachexia; sepsis; trauma associated with burns, malnutrition, and stress; aging; lupus and other autoimmune diseases; endocrine disease; hyperuricemia, polycystic ovary syndrome and complications arising from athletic activity.

15 Claims, 2 Drawing Sheets

5,827,896

PINITOL AND DERIVATIVES THEREOF FOR THE TREATMENT OF METABOLIC DISORDERS

This application is a continuation-in-part of U.S. Ser. No. 08/407,430, filed Mar. 17, 1995, now Pat. No. 5,550,166.

This invention was made with government support under grant Nos. DK 20579 and RR 00954 awarded by the National Institutes of Health. The U.S. government has certain rights in the invention.

SUMMARY OF THE INVENTION

The invention relates to pinitol and derivatives and metabolites thereof and compositions containing same for lowering plasma free fatty acids levels and for treating conditions associated with insulin resistance. These conditions associated with insulin resistance can result from disorders such as diabetes mellitus and its chronic complications; obesity; hyperlipidemias and dyslipidemias; atherosclerosis; hypertension; cardiovascular disease; AIDS; cancer; wasting/cachexia; sepsis; trauma associated with burns, malnutrition, and stress; aging; lupus and other autoimmune diseases; endocrine disease; hyperuricemia, polycystic ovary syndrome and complications arising from athletic activity or inactivity.

The compositions of the invention are preferably in a dosage form providing from 0.1 milligram to 1.0 grams per day of the pinitol, derivative or metabolite thereof per kilogram body weight of a mammal. The compositions can be administered orally, enterally, or intravenously and are effective in lowering plasma free fatty acids, glucose, insulin and lipid levels. A method is also provided for obtaining pinitol from soy fractions.

BACKGROUND OF THE INVENTION

Figure 1:
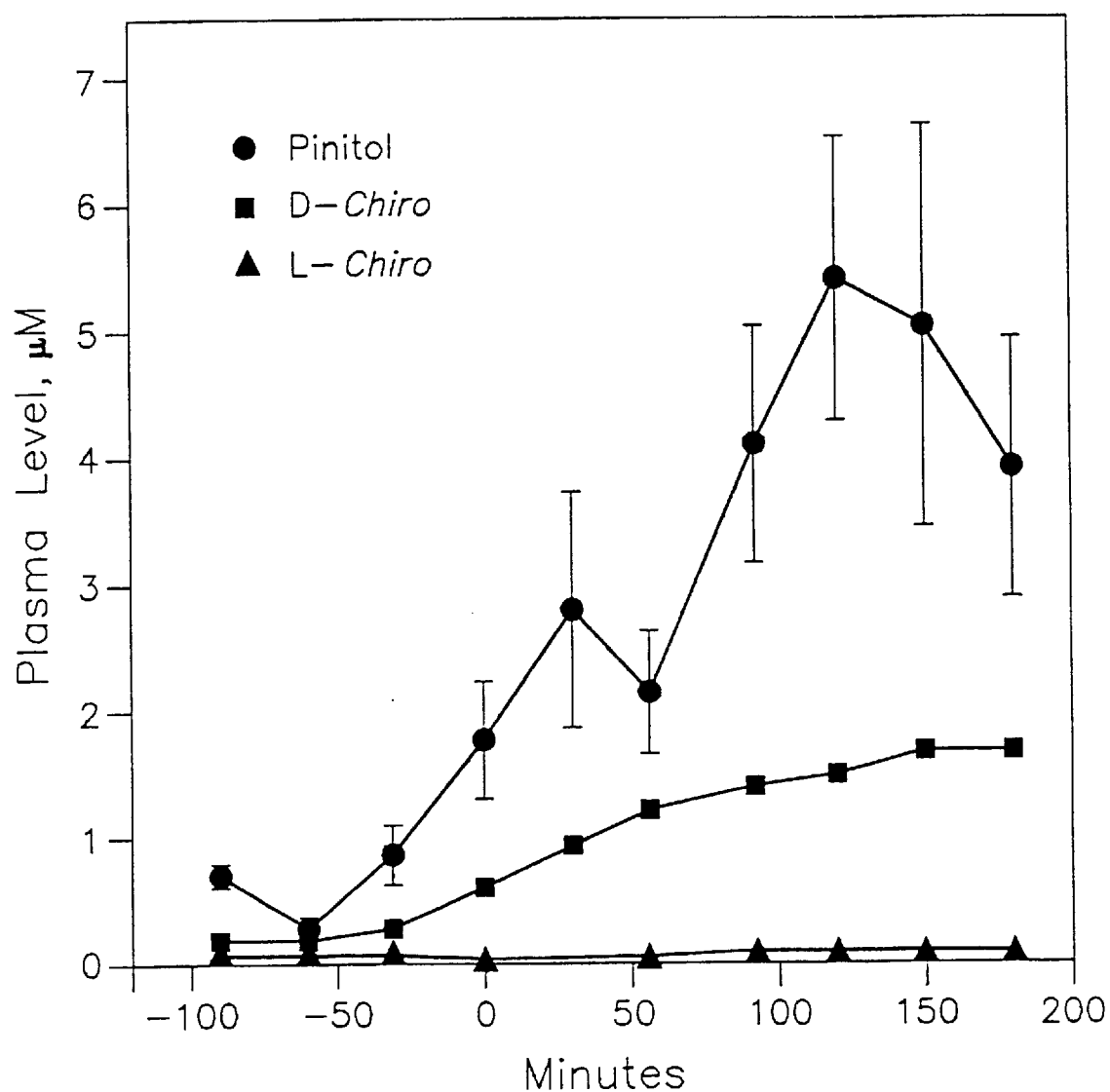
FIG. 1 shows average plasma levels of pinitol, D-chiro-inositol, and L-chiro-inositol for non-insulin-dependent Type II diabetics fed a pinitol fraction derived from soy.

Insulin is the major anabolic hormone in the body and has multiple effects on a variety of tissues. The actions which are most familiar are its ability to stimulate the uptake of glucose into insulin-sensitive tissues such as muscle and fat and to inhibit the release of glucose from the liver. In addition, insulin regulates both plasma and tissue lipid metabolism, protein turnover, cell growth and electrolyte balance. Insulin acts by binding to a specific receptor on the cell membrane, which is a glycoprotein consisting of two alpha and two beta subunits. Binding of insulin to the alpha subunit activates autophosphorylation of the beta subunit, which then becomes an active tyrosine kinase. By phosphorylating tyrosine residues of other proteins the activated insulin receptor initiates a cascade of biochemical effects. A complete understanding of insulin actions and identification of mediators has yet to be elucidated.

However, even though insulin is essential for life, excessive levels of plasma insulin are frequently observed in insulin-resistant disorders and are closely associated with harmful effects. These include increased cardiovascular disease, atherosclerosis, reduced high density lipoprotein (HDL) cholesterol, elevated plasma triglycerides and low density lipoprotein (LDL) cholesterol, hypertension, abdominal obesity, and decreased plasma fibrinolytic activity. Thus, it is sometimes desirable to control or reduce plasma insulin levels.

Since elevated plasma insulin levels reflect resistance to insulin, reduction of plasma insulin can be achieved if sensitivity to insulin is improved. Past studies suggest that some of the actions of insulin may be mediated through inositol phosphoglycan molecules released from cell membranes in response to insulin. Augmenting the release of these molecules is one way to improve insulin sensitivity. The inositol phosphoglycans are small molecules of approximately 1500 daltons which are cleaved from inositol phospholipids by phospholipases. Inositol is a key component of the insulin-related phosphoglycans and almost all of the inositol in mammals in myo-inositol. However, D-chiro-inositol was found after 6N HCl hydrolysis to be the sole or predominant inositol in some of the inositol phosphoglycans analyzed. This finding led to the measurement of D-chiro-inositol in diabetic tissues and fluids. The results showed reduced tissue and urinary levels of D-chiro-inositol (Kennington, A. S., Hill, C. R., Craig, J., Bogardus, C., Raz, I., Ortmeyer, H. K., Hansen, B. C., Romero, G., Larner, J. 1990. Low urinary chiro-inositol in non-insulin-dependent diabetes mellitus. N. Engl. J. Med. 323:373–378). These results suggest a rationale for the treatment of diabetic and insulin-resistant patients with D-chiro-inositol as proposed in U.S. Pat. No. 5,124,360. In later work with improved analytical technique, an increased excretion of urinary D-chiro-inositol was demonstrated (Ostlund, R. E., Jr., McGill, J. B., Herskowitz, I., Kipnis, D. M., Santiago, J. V., Sherman, W. R. 1993. D-chiro-inositol Metabolism in Diabetes Mellitus. Proc. Natl. Acad. Sci. USA 90:1988–1992). Thus, prior work left open issues regarding tissue levels or excretion of the possible insulin mediator, and focused only on the hydrolysis product D-chiro-inositol.

Prior art is also handicapped by lack of knowledge concerning the exact structure of inositol phosphoglycan insulin mediator molecules and by lack of knowledge of the distribution of chiro-inositol-like substances in foods and body fluids. Pinitol is a methyl ether of D-chiro-inositol and is readily hydrolyzed to D-chiro-inositol. Pinitol is known to be contained in pine wood and in legumes. A pinitol-like substance of undisclosed structure extracted from Bougainvillea spectabilis was found to lower the blood glucose of both normal and alloxan-treated insulin-deficient mice at a minimum dosage level of 0.01 g/kg (Narayanan, C. R., Joshi, D. D., Mujumdar, A. M., Dhekne, V. V. 1987. Pinitol—A new anti-diabetic compound from the leaves of Bougainvillea spectabilis. Current Science 56:139–141). The effectiveness of pinitol for the treatment of insulin resistant conditions, especially those of humans, was unknown until the present invention. Prior art exemplified by U.S. Pat.No. 5,124,360 has focused on pinitol as a manufacturing source of D-chiro-inositol where D-chiro-inositol could be liberated from pinederived pinitol using the severe conditions of concentrated hydrogen iodide hydrolysis at high temperature rather than on the direct use of pinitol in medical applications. The same reference incorrectly identifies pinitol as an ester rather than an ether of D-chiro-inositol.

Phillips, et al., J. Agric. Food Chem., Vol. 30, pp. 456–466 (1982) describes various cyclitols present in soybean plants. Philip Nordin, Plant Physiol., Vol. 76, pp. 313–315 (1984) describes preferential leaching of pinitol from soybeans during imbibition. A. E. Smith, et al., Crop Science, Vol. 20, pp. 75–77 (1980) describes the occurrence of pinitol in the foliage of several forage legume species.

U.S. Pat. No. 5,124,360 describes administration of a supplement for the therapeutic treatment of insulin-resistant type II diabetes comprising D-chiro-inositol. U.S. Pat. No. 5,091,596 describes a method of producing D-chiro-inositol from Kasugamycin or pinitol which were considered as precursors to D-chiro-inositol and not used for treatment purposes. The preparation of D-chiro-inositol from Kasugamycin is a much more difficult process than that from soy as carried out by the present invention.

Y. Pak, et al., The Journal of Biological Chemistry, Vol. 267, No. 24, pp. 16904–16910 (August 1992) describes the in vivo conversion of myoinositol to chiroinositol in rat tissues.

The present invention shows for the first time that insulin resistance in humans is directly treatable by pinitol. This result is unexpected based on prior art in the Type I insulin deficient diabetic (alloxan-treated) rat model. The present invention demonstrates that human Type II diabetics effectively respond to pinitol and that insulin and glucose levels and plasma free fatty levels are decreased by pinitol.

It is an object of the present invention to provide compositions comprising an effective amount of pinitol or a derivative or metabolite thereof for treating conditions associated with insulin resistance. These include disorders such as diabetes mellitus and its chronic complications; obesity; hyperlipidemias and dyslipidemias; atherosclerosis; hypertension; cardiovascular disease; AIDS; cancer; wasting/cachexia; sepsis; trauma associated with burns, malnutrition, and stress; aging; lupus and other autoimmune diseases; endocrine disease; hyperuricemia, polycystic ovary syndrome and complications arising from athletic activity or inactivity. It is also an object of this invention to provide compositions comprising an effective amount of pinitol or a derivative or metabolite thereof for lowering plasma free fatty acids levels.

It is a further object of this invention to provide methods for lowering plasma free fatty acids and for treating conditions of insulin resistance in mammals comprising administering an effective amount of pinitol or a derivative or metabolite thereof, orally or intravenously, as a nutritional supplement or medicament. It is an even further object of this invention to provide a method for obtaining and purifying pinitol from soy fraction.

DETAILED DESCRIPTION

This invention relates to a composition useful in lowering plasma free fatty acids levels and in treating conditions of insulin resistance in mammals (preferably homo sapiens) comprising an effective amount of pinitol or a derivative or metabolite thereof. Pinitol and derivatives and metabolites thereof are useful in nutritional and medicinal compositions according to the present invention for lowering plasma free fatty acids levels and in treating conditions associated with insulin resistance. These include disorders such as diabetes mellitus and its chronic complications; obesity; hyperlipidemias and dyslipidemias; atherosclerosis; hypertension; cardiovascular disease; AIDS; cancer; wasting/cachexia; sepsis; trauma associated with burns, malnutrition, and stress; aging; lupus and other autoimmune diseases; endocrine disease; hyperuricemia, polycystic ovary syndrome and complications arising from athletic activity or inactivity.

Pinitol has the chemical structure given below:

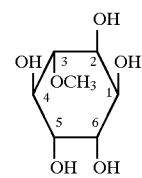

Suitable derivatives and metabolites of pinitol include pinitol glycosides, pinitol phospholipids, esterified pinitol, lipid-bound pinitol, pinitol phosphates and pinitol phytates and mixtures thereof.

Pinitol and its derivatives or metabolites are available from a number of natural sources (such as, for example, pine needles, chick peas, Bougainvillea leaves, alfalfa, soy beans and other legumes) and synthetic processes, but preferably is obtained from soy fractions. The present invention also provides a method of obtaining pinitol in relatively high yield and purity from soy fractions comprising the steps of:

a) removing protein from said soy fraction, b) treating said deprotenized soy fraction from a) with activated charcoal, c) treating the resultant soy material from b) with ion exchange resins to deionize said material, d) removing unwanted, non-inositol sugars from the material from c) by contacting said material with a hydroxide form anion exchange resin, and e) recovering said pinitol.

The compositions of this invention provide an effective amount of pinitol or derivatives or metabolites thereof in a dosage form for administration to mammals for lowering plasma free fatty acid levels and for treating conditions of insulin resistance. The compositions can be administered orally, enterally or intravenously. Without being bound by any theory, it appears that pinitol is readily absorbed in vivo and metabolized. The compositions are also effective in improving insulin sensitivity associated with hyperinsulinemia and impaired glucose tolerance. The compositions are also effective in lowering plasma glucose levels, plasma insulin levels and plasma lipid levels.

Fatty acids are found in all plasma lipid classes such as low density lipoprotein (LDL), high density lipoprotein (HDL), phospholipids and triglycerides in which they are attached by an ester linkage to glycerol and other molecules. However, there is a fraction of plasma fatty acids that is not so esterified and this fraction exists as free fatty acid anions (referred to herein as plasma free fatty acids) and is mostly bound to plasma albumin.

Free fatty acids are believed to be important in the generation of insulin resistance. Without being bound by any theory, the postulated sequence of events is as follows. Normally insulin reduces plasma free fatty acid levels but this is blunted in patients with obesity or diabetes. The resulting elevated free fatty acids then further impair the ability of the liver and other organs to use glucose. The extent to which this pathway operates is not known exactly. Lowering of plasma free fatty acids by pinitol or its derivatives or metabolites are believed to be effective in the treatment of diabetes mellitus or insulin resistance.

Preferably the compositions of this invention are in a dosage form, either single or multiple, which provides from 0.1 milligram to 1 gram, more preferably 1 to 10 milligrams, per day of pinitol or derivative or metabolite per kilogram body weight of the mammalian subject to which the composition is being administered. The composition can be in the form of an orally ingestible nutritional supplement. This nutritional supplement can be in a variety of forms such as a free-flowing powder, bar, tablet, capsule or other solid dosage form; or liquid forms, such as an aqueous-based oral, enteral or intravenous solution, dispersion or emulsion.

For example, an enteral composition of the present invention preferably comprises deionized water, pinitol, maltodextrin, sodium caseinate, corn syrup solids, medium chain triglycerides, canola oil, calcium caseinate, soy protein, potassium citrate, magnesium chloride, sodium citrate, tricalcium phosphate, soy lecithin, sodium ascorbate, choline chloride, potassium chloride, vitamin E, molybdenum yeast, selenium yeast, carrageenan, chromium yeast, biotin, niacinamide, zinc sulfate, ferrous sulfate, calcium pantothenate, vitamin A, cyanocobalamin, manganese sulfate, copper gluconate, vitamin K, thiamin, pyridoxine hydrochloride, vitamin D, riboflavin, folic acid, potassium iodide, antifoam agents and natural or artificial flavors and sweeteners. Ingredients which may also be added to enteral compositions of this invention include fructose, soybean oil, sunflower oil, canola oil, carnitine, taurine, and other natural components such as beef, peach puree, peas, green beans and orange juice.

Orally ingestible compositions of this invention preferably contain pinitol, water, maltodextrin, sugar, corn oil, sodium caseinate, soy protein isolate, calcium caseinate, potassium citrate, tricalcium phosphate, magnesium chloride, sodium citrate, lecithin, potassium chloride, choline chloride, ascorbic acid, potassium hydroxide, carrageenan, vitamin E, carrageenan, zinc sulfate, ferrous sulfate, niacinamide, biotin, vitamin A, calcium pantothenate, copper gluconate, cyanocobalamin, manganese sulfate, vitamin K, potassium iodide, and natural and artificial flavors. Orally ingestible compositions in dry powder form preferably contain pinitol, nonfat dry milk, sugar, cocoa, carrageenan, polysorbate 80, magnesium oxide, salt, vanillin, vitamin E, ascorbic acid, ferric orthophosphate, zinc sulfate, vitamin A, niacinamide, maltol, copper gluconate, calcium pantothenate, pyridoxine hydrochloride, thiamine, cyanocobalamin, vitamin $D_3$, folic acid, riboflavin, biotin, and natural and artificial flavors. This dry powder can be mixed with milk or water prior to consumption. Another preferred powder composition for oral consumption includes maltodextrin, pinitol, citric acid, calcium hydroxide, salt, aspartame, ascorbic acid, potassium citrate, orange juice solids, vitamin E, polysorbate 60, zinc sulfate, ferrous sulfate, biotin, niacinamide, copper gluconate, calcium pantothenate, cyanocobalamin, vitamin $D_3$, folic acid, pyridoxine hydrochloride, riboflavin, and natural and artificial flavors and coloring. Ingredients can also include magnesium gluconate, dipotassium phosphate, magnesium sulfate trihydrate, manganese sulfate monohydrate, and thiamine. This powder composition can be mixed with water or fruit juices prior to consumption. Another preferred powder composition comprises pinitol with a dextrose or maltodextrin carrier which can be added to food and juices.

A preferred composition of this invention in the form of a nutritional bar comprises pinitol, raisins, diced nuts, pineapple, guar gum, protein mixture, fructose, caramel, honey, high maltose corn syrup, lecithin, soya bean oil, salt, magnesium oxide, vitamins and minerals, and natural and artificial flavorings and coloring.

Suitable intravenous solutions for use according to the present invention comprise pinitol, or a derivative or metabolite thereof, in a sterile liquid carrier such as water or 1,3-butanediol.

The various compositions of the invention can also contain other conventional ingredients such as suspending or wetting agents, preservatives, antioxidants, thickening agents and the like.

The compositions of the present invention are useful in methods of lowering plasma free fatty acid levels and treating insulin resistance in mammals, particularly homo sapiens, comprising administering an effective amount of pinitol or a derivative or metabolite thereof. The pinitol or derivative or metabolite thereof is preferably administered as multiple doses or continuous doses for a period of 1 day or longer; more preferably 3 days or longer. The effective amount of said pinitol or derivative or metabolite thereof for use in the method of this invention is preferably 0.1 mg to 1.0 grams per day per kilogram of body weight, and is preferably administered orally.

The present invention also relates to a method of obtaining pinitol from soy fraction as described earlier.

The soy fractions used in this method preferably comprise soy solubles, soy whey, and mixtures thereof. The method yields a recovered product which is about 20% or more, preferably 50% or more, pinitol on a dry weight basis.

Soluble fractions derived from soy protein production contain D-chiro-inositol at approximately 4% of dry weight, and most of this is in the form of pinitol (3-O-methyl-D-chiro-inositol). It is desirable to purify this material to at least 50% of dry weight for medical food use. Preferably, soy solubles or other fractions are first deproteinized and treated with activated carbon to prepare them for column chromatography. Then the material is deionized preferably by passage over a cation exchange column followed by an anion exchange column. Unwanted non-inositol sugars are removed on a hydroxide-form strong base anion exchange resin. The final fraction not binding to the column contains pinitol at about 20% (preferably 50%) by weight or more based on total weight of the final fraction.

It is important to separate the ion exchange and sugar removal processes. The removal of ions and unwanted sugars by hydroxide-form anion exchange chromatography occurs by different mechanisms. Anion removal results from binding of sample anions to the column and their replacement in the solution by hydroxide ions. In contrast, sugar binding to strong ion exchange columns is an adsorptive process in which no hydroxide is released from the ion exchange resin. Under many conditions ions and sugars compete with each other and mutually reduce the efficiency of purification.

For example, anion removal results in release of hydroxide ions and results in operating pH levels of 12–13. However, this pH inhibits sugar binding since sugars can be partially or completely removed from anion exchange columns by 0.01N or stronger NaOH. Conversely, sugar binding to anion exchange columns competes with anion removal if both sugars and salts are presented at the same time in neutral solutions. In the new process ions are removed first followed by removal of sugars. In order to ensure complete deionization the material is passed over a cation exchanger in the hydrogen form to create a decationized stream with pH about 1–2. When subsequently passed over a hydroxide from anion exchanger the acidic pH drives deionization to completion despite the presence of sugars. The deionized material is then further purified in the absence of ions.

The affinity of hydroxide-form anion exchangers for unwanted sugars is relatively low so that longer contact time with the column is needed for efficient sugar adsorption than for deionization. In addition, under conditions of high column load the unwanted sugars "bleed" from the column and reduce the purification achieved.

Deproteinization and charcoal treatment of the sample before ion exchange treatment is important to avoid column fouling, on-column precipitation and alteration of sugar-binding properties of the resin.

The pinitol recovered from this process can be used according to the present invention in a variety of applications as described herein. The pinitol can also be converted to D-chiro-inositol, such as by hydrolysis.

A preferred method for obtaining pinitol from soy fractions is as follows:

I. Deproteinization and charcoal treatment

1. Acid precipitation of soy solubles. To 100 ml of soy solubles after ethanol removal from the soy solubles fraction is added 0.4 ml 12N HCl and 2.5 g activated carbon (Darco KB). The resulting pH is 3.95. After 1 hr the material is centrifuged at 1000×g for 10 minutes and filtered. The clear, colorless supernatant is applied to the ion exchange columns. This step removes both proteins and lipids which foul the chromatography columns. Heat treatment at 60–90° C. or even autoclaving at 121° C. for 4 hr does not quantitatively remove proteins and precipitation on the columns is observed during subsequent ion exchange chromatography. Charcoal treatment is not needed for decolorization (the columns will completely remove the slight yellow color present in the acid precipitation supernatant), but it is essential to remove other materials that will adhere to the anion exchange resin, resist removal by acid or base treatment, and significantly slow the rate of unwanted sugar removal. Residual charcoal can be removed by filtration through a 0.22 micron particulate filter, but this step is not routinely necessary. The yield is 82 ml of supernatant. The acid pH acts as a preservative so that the sample can be kept refrigerated for months.

2. Ultrafiltration. Ultrafiltration completely removes proteins. However, it is still essential to treat the permeate with charcoal to avoid column fouling. If ultrafiltration is used the permeate should be concentrated to about 5–10% solid before the next step.

II. Deionization

The resins used in this invention are commercially available ion exchange resins, such as, for example, IR-120+(a strong acid cation exchanger) and IRA-400-OH (a strong base anion exchanger). These comply with FDA regulations for ion exchangers used in food processes and are made by Rohm and Haas. However, any similar resins can be substituted.

Deionization is done before sugar removal. Since soy solubles have relatively few ions, only a relatively small amount of deionization resins are needed. The exact equivalence of the resins with respect to acid-precipitated, charcoal-treated soy solubles (from step I above) determined by titration is as follows:

1. Cation Exchange 13.1 ml soy solubles/ml wet resin
2. Anion Exchange 9.8 ml

In the examples calculated below it is assumed that sample equivalent to only 80% of this capacity is applied. The soy solubles are applied first to the cation exchange column and then to the anion exchange column. Although precipitation does not occur, our preference is for 80 micron retaining netting on the columns. This is somewhat larger than the approximately 30 micron netting normally used and it essentially eliminates any possibility of column clogging after prolonged use or in the presence of precipitate.

It is possible that deionization could be done by batch. However, batch processing is not as efficient as column methods, regeneration of the resin is harder, and the deionization process takes much longer, for example, gentle swirling of the sample. It is recommended rotating the sample with each resin for at least 6 hours. The efficiency of ion removal can be monitored by conductivity measurements. The applied material has a conductivity of 8070 $\mu$ohm and in adequately deionized material this is reduced to less than 100 $\mu$ohm. With batch deionization incomplete ion removal was observed with a final conductivity of 1100 $\mu$ohm.

The columns are regenerated in standard fashion with about 3 column volumes of 1.5N HCl or 1.0N NaOH followed by water washes.

III. Sugar Removal on Anion Exchange Column

Sugars other than pinitol and other inositols are adsorbed to IRA-400-OH anion exchange resin. If the applied sample is not adequately deionized, hydroxide ions will be released and this will inhibit sugar binding to the resin.

1. Amount of resin needed. Adequate sugar removal requires 2.5 ml resin per ml of soy solubles from step II above. Thus, this step will require more column capacity than deionization.

2. Technique of chromatography. 1 ml of deionized material is applied to a 2.5 ml column at 0.1 ml of column volume/minute and recycled three times. The adsorption process is slow and incomplete adsorption is often seen with one column passage. The efficiency of sugar removal varies as the column ages, but three passes over the column are sufficient even for older columns. The column is then washed with 1.2 ml of water to yield 85% of the applied pinitol. Further washing is counterproductive in that a small amount of contaminating carbohydrate desorbs from the column over time whereas very little pinitol is removed. In fact, this desorption becomes limited as more sample is applied to the column.

The purification process can be monitored visually. A fresh column is orange-brown in color and translucent. With sugar binding it becomes dark brown and opaque, beginning at the top of the column. The effective column capacity is reached when the dark area progresses about ⅔ of the way down the column. After regeneration (described below) the column assumes the original color.

3. Concentration. The final material is at a concentration of about 1 mg/ml and preferably should be concentrated to about 100 mg/ml, which is suitable for formulation.

4. Temperature control. Adsorptive processes in general are most efficient in the cold and are inhibited at elevated temperatures. The methods described here work sufficiently at room temperature. However, at 4°, compared to room temperature, the removal of unwanted carbohydrate is increased 8% and the column "bleed" is reduced 31%. This slight advantage is probably not of importance. However, at 60°, the highest temperature at which the hydroxide form anion exchange resins are stable, the column "bleed" is increased about 200%. From an operational standpoint, cooler temperatures help marginally and temperatures above ambient should be avoided.

5. Regeneration of the column. The column is washed in the reverse direction with 2.5 volumes of 1N NaOH and then with water.

The following examples are presented to demonstrate the invention. The examples are intended to be illustrative and not limitative.

EXAMPLE 1

This example identifies food sources of D-chiro-inositol-like compounds and shows that alfalfa and soybeans are rich in the material, which is present in the form of pinitol rather than as free D-chiro-inositol.

The highly standardized components of Purina Rodent Chow 5001 were analyzed by gas chromatography-mass spectrometry after hydrolysis in 6N HCl at 110° for 24 hr. to convert the pinitol to D-chiro-inositol and the results are presented in Table I below:

TABLE 1

| Component | D-chiro-inositol nMol/mg dry weight |
|---|---|
| Alfalfa | 74.7 ± 5.2 |
| Soybean Meal | 54.1 ± 4.1 |
| Wheat Germ | 1.011 ± 0.008 |
| Ground Oats | 0.758 ± 0.028 |
| Fish Meal | 0.676 ± 0.012 |
| Ground Beet Pulp | 0.248 ± 0.003 |
| Meat Meal | 0.058 ± 0.004 |
| Yeast | 0.049 ± 0.014 |
| Midds | 0.049 ± 0.015 |
| Ground Corn | 0.044 ± 0.003 |
| Bleachable Fat | 0.018 ± 0.001 |
| Molasses | 0.010 ± 0.004 |
| Whey | 0.009 ± 0.001 |

These results show that legumes have a large content of pinitol whereas other foods contain relatively little. Soybean meal is about 1% D-chiro-inositol-like compounds by dry weight. However, data shows that very little of the D-chiro-inositol-like compounds in the soy material is free D-chiro-inositol. After purification as described below 83% of the D-chiro-inositol like compounds was pinitol as determined by gas chromatographic retention time and mass spectrum when compared to authentic pinitol prepared from pine sawdust.

Pinitol was present only in samples which had not been subjected to acid hydrolysis and was quantitatively converted to D-chiro-inositol after hydrolysis for 24 hr at 110° in 6N HCl. This shows that 6N HCl cleaves not only phosphate bonds of inositol phosphates but also the ether linkage of pinitol. In contrast to other ether linkages it is not necessary to use concentrated hydrogen iodide to convert pinitol to D-chiro-inositol as detailed in U.S. Pat. No. 5,091,596.

EXAMPLE 2

This example illustrates the production of an enriched pinitol from soybeans.

Soy whey after precipitation of protein isolate at acid pH was found to contain 2.4% total D-chiro-inositol (bound and free, measured after acid hydrolysis) by dry weight. This material was spray-dried and resuspended at a concentration of 25% solids. After centrifugation and filtration it was autoclaved and then the supernatant was applied to an IRA 400 hydroxide form anion exchange column in an amount equal to half the column bed volume followed by a similar IR120+hydrogen-form cation exchange column. The final material was concentrated by evaporation, treated with charcoal, and autoclaved. The average total D-chiro-inositol content after acid hydrolysis was 22.5% by weight and 83% of this was originally in the form of pinitol. This material was used for the experiments in Example 3.

EXAMPLE 3

This example shows that feeding of a pinitol fraction derived from soy to human non-insulin-dependent Type II diabetics results in increased plasma levels of pinitol and D-chiro-inositol and reduction in plasma insulin and glucose levels.

Five non-insulin-dependent diabetic subjects were studied on two occasions one week apart. For three days the subjects received pinitol 4.15 mg/kg/day orally in a drink once daily for 3 days. The preparation also contained 0.85 mg/kg/day D-chiro-inositol in other forms. The total inositol content by weight (including pinitol) was 22.5%. On the fourth day they took no morning dose of oral hypoglycemic agents and reported to the Clinical Research Center. Baseline blood samples were taken at −90 and −60 minutes, and at −60 minutes a dose of pinitol identical to that taken during the previous 3 days was given orally. The material contained less than 5 calories. At zero time 75 g glucose was given to begin a glucose tolerance test and blood samples were taken half-hourly for 3 hours. In random order the subjects received either myo-inositol (5 mg/kg/day) or soy pinitol (total inositol content 5 mg/kg/day). Myo-inositol has no definite effect on plasma glucose or insulin and was included as a control. Plasma inositol levels were measured by gas chromatography/mass spectrometry and insulin levels were measured by RIA.

Plasma inositol levels changed little after feeding myo-inositol during the control glucose tolerance tests. However, the plasma pinitol and D-chiro-inositol levels rose by over 10-fold during pinitol feeding as shown in FIG. 1. Plasma pinitol peaked at 5.4 $\mu$M three hours after the oral administration of pinitol whereas plasma D-chiro-inositol levels were lower at all time points and had reached 1.7 $\mu$M four hours after dosing. The preponderant effect of soy pinitol feeding, therefore, was to raise plasma pinitol levels.

Figure 2:
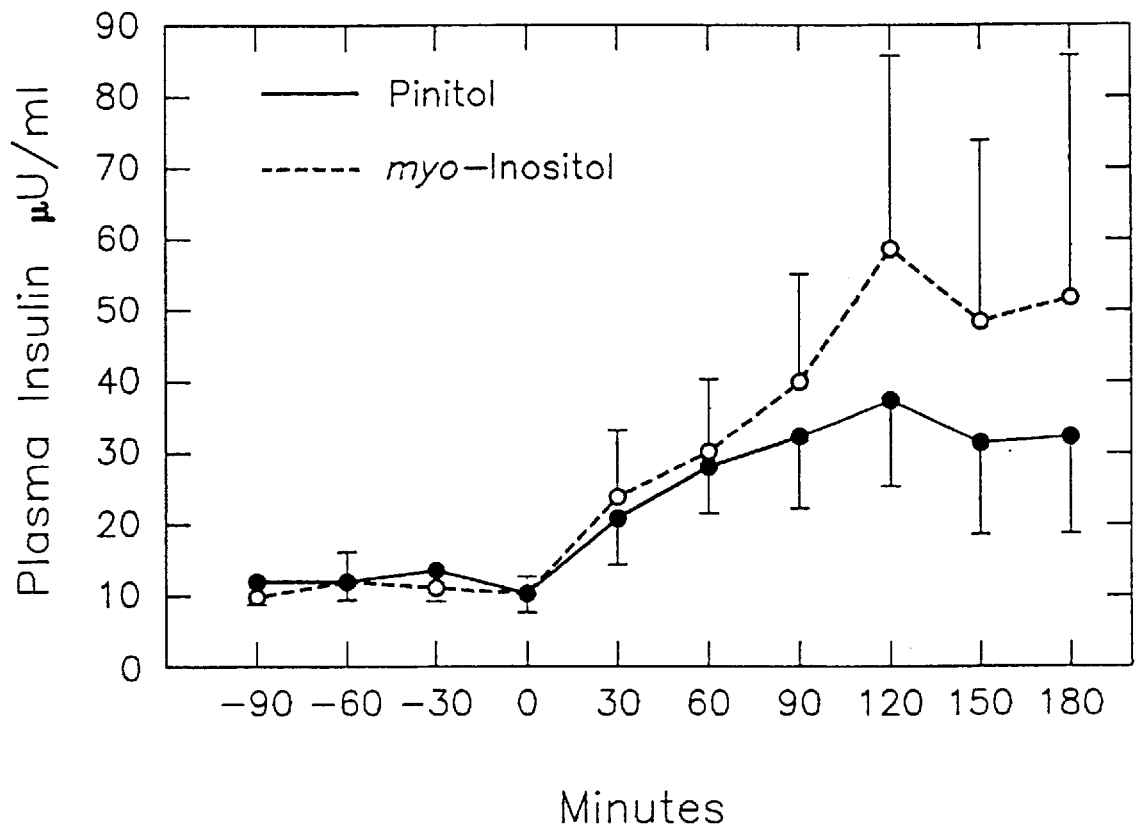
FIG. 2 shows average plasma insulin levels for the diabetics fed pinitol compared to myo-inositol.

A significant reduction in plasma insulin during the glucose tolerance test was observed during pinitol treatment as shown in Table 2 and FIG. 2. Baseline insulin and glucose levels were unchanged, but there was a significant reduction in insulin during the glucose tolerance test, which began at time 0. Insulin area ($\mu$U/ml insulin×minutes) was lowered by 25.2±8.9%, p=0.046:

TABLE 2

| | Insulin Area ($\mu$U/ml × minutes) | | |
|---|---|---|---|
| Subject | Pinitol | myo-Inositol | Percent Change (Reduction) |
| 1 | 8844 | 18066 | 51.1 |
| 2 | 4032 | 4599 | 12.3 |
| 3 | 1518 | 2253 | 32.6 |
| 4 | 1566 | 2256 | 30.6 |
| 5 | 1197 | 1191 | 0.5 |

There was also a reduction in plasma glucose area (mg/dl×minutes) during the glucose tolerance test of 18.8±9.1%, p=0.11.

EXAMPLE 4

This example shows that plasma D-chiro-inositol is closely related to plasma triglycerides and high density lipoprotein cholesterol in diabetic subjects.

Nineteen insulin-dependent diabetic subjects and 54 non-insulin-dependent diabetics were studied in a cross-sectional analysis of the determinants of plasma triglyceride and high density lipoprotein cholesterol levels. The age, gender, body mass index, concomitant drug therapy, glycated hemoglobin, and plasma insulin were measured as covariates known to influence plasma lipids and lipoproteins. Plasma D-chiro-inositol was measured and all values were used in multiple regression equations to predict plasma triglyceride and high density lipoprotein cholesterol. The following statistical associations were found:

| Dependent Variable | Predictive Variables | Statistical Significance | $R^2$ of Model |
|---|---|---|---|
| Insulin-Dependent Diabetes | | | |
| Plasma Triglycerides | D-chiro-inositol | <0.0001 | 0.683 |
| | Glycohemoglobin | 0.003 | |
| | Insulin Dose | 0.04 | |
| Plasma HDL Cholesterol | D-chiro-inositol | 0.005 | 0.632 |
| | Gender | 0.021 | |
| Non-Insulin-Dependent Diabetes | | | |
| Plasma Triglycerides | D-chiro-inositol | 0.0005 | 0.240 |
| | Glycohemoglobin | 0.025 | |
| Non-Insulin-Dependent Diabetics with Glycohemoglobin > 10 | | | |
| Plasma Triglycerides | D-chiro-inositol | 0.0001 | 0.623 |
| | Glycohemoglobin | 0.0076 | |
| | Insulin | 0.032 | |

(R is multiple correlation coefficient)

These data show that plasma D-chiro-inositol was the strongest independent predictor of plasma triglycerides in both insulin-dependent and non-insulin-dependent diabetics and was the strongest predictor of high density lipoprotein cholesterol in insulin-dependent diabetic subjects. There can be a component of insulin resistance in insulin-dependent diabetic subjects.

EXAMPLE 5

This example shows that plasma free fatty acids are reduced in humans by administration of pinitol.

10 non-insulin-dependent diabetes patients maintained a pinitol and D-chiro-inositol-deficient diet (no legumes, or citrus fruits) throughout the study. The NIDDM subjects were recruited who were metabolically stable, were not taking insulin, had glycated hemoglobin values between 6.5–15, were not taking medication that interferes with glucose metabolism, had normal liver and kidney function and had a BMI less than 37 kg/m². The following table summarizes the characteristics of the patients.

| | mean ± SD |
|---|---|
| Number | 10 |
| Age, years | 62.1 ± 7.6 |
| Gender, men/women | 7/3 |
| Race, white/black | 9/1 |
| Sulfonylurea treatment, yes/no | 8/2 |
| Height, cm | 171.6 ± 9.4 |
| Weight, kg | 91.4 ± 17.7 |
| BMI, kg/m² | 31.0 ± 4.9 |
| Glycated hemoglobin, % | 10.3 ± 44 |
| Fasting plasma glucose, mg/di | 173 ± 44 |

Each subject received both placebo and soy-derived pinitol in separate tests. After an initial 5-day washout period the subjects received 5 days of treatment with either pinitol 5 mg/kg BID (total dose 10 mg/kg/day) or placebo without inositols. The material was given orally in 60 ml. calorie-free KOOL-AID drink.

Twelve hours after the last dose, two fasting plasma samples were drawn from each subject 15 minutes apart. Plasma free fatty acid levels were measured. A dose of pinitol was then given and a 3-hour glucose tolerance test was performed.

After a second 5-day washout period and another 5 days of pinitol or placebo feeding the testing was repeated. The order of treatment (pinitol or lacebo) was randomized and study investigatyors and those conducting the analyses were blinded to the order of treatment given.

The results of the study are given below:

| | Placebo | Pinitol Mean ± SD | P-value |
|---|---|---|---|
| Fasting plasma free fatty acids ($\mu$M) | 648 ± 244 | 569 ± 276 | 0.05 |
| Fasting plasma pinitol ($\mu$M) | 0.014 ± 0.012 | 0.488 ± 0.290 | <0.0001 |
| Fasting plasma chiro-inositol ($\mu$M) | 0.115 ± 0.123 | 0.633 ± 0.855 | <0.0001 |

Plasma pinitol and chiro-inositol were increased substantially by pinitol feeding as compared to the pinitol-deficient diet. Pinitol treatment was associated with a statistically significant reduction of 12.2% in mean fasting plasma free fatty acids (p=0.05 by paired t-test). When the repeated fasting plasma free fatty acid measurements were subjected to analysis of variance the reduction with pinitol treatment was highly significant (p=0.004). There was also a significant inverse relation between change in fasting plasma free fatty acids with pinitol feeding and the fasting plasma pinitol level achieved during pinitol feeding (r=0.660, p=0.038). Change in baseline plasma free fatty acids seems to be an important indicator of physiologic improvement since it was correlated with change in glucose area during a 3-hr glucose tolerance test (r=0.748, p=0.013).

We claim:

1. A composition comprising an effective amount of pinitol or a derivative or metabolite thereof in a dosage form effective in lowering plasma free fatty acid levels in a mammal.

2. The composition of claim 1 wherein said dosage form is an orally ingestible nutritional supplement.

3. The composition of claim 1 wherein said dosage form is an orally ingestible medicament.

4. The composition of claim 1 wherein said dosage form is a liquid suitable for intravenous injection.

5. The composition of claim 1 wherein said dosage form provides 0.1 milligram to 1.0 gram/day of said pinitol, derivative or metabolite thereof per kilogram of body weight of said mammal.

6. The composition of claim 5 wherein said dosage form provides 1 to 10 milligrams/day of said pinitol, derivative or metabolite thereof per kilogram of body weight of said mammal.

7. The composition of claim 1 wherein said pinitol, derivative or metabolite thereof is selected from the group consisting of pinitol, pinitol glycosides, pinitol phospholipids, esterified pinitol, lipid-bound pinitol, pinitol phosphates and pinitol phytates and mixtures thereof.

8. A method of lowering plasma free fatty acids levels in a mammal comprising administering an effective amount of pinitol or a derivative or metabolite thereof.

9. The method of claim 8 wherein said mammal is a homo sapien.

10. The method of claim 8 wherein said effective amount is 0.1 milligram to 1.0 grams per kilogram of body weight per day.

11. The method of claim 8 wherein said effective amount is 1 to 10 milligrams per kilogram of body weight per day.

12. The method of claim 8 wherein pinitol or derivative or metabolite is administered orally.

13. The method of claim 8 wherein said pinitol, derivative or metabolite thereof is selected from the group consisting of pinitol, pinitol glycosides, pinitol phospholipids, esterified pinitol, lipid-bound pinitol, pinitol phosphates and pinitol phytates and mixtures thereof.

14. The method of of claim 8 wherein said pinitol, or derivative or metabolite thereof is administered as multiple doses or continuous doses for a period of 1 day or longer.

15. The method of claim 8 wherein said pinitol, derivative or metabolite thereof is administered as multiple doses or continuous doses for a period of 3 days or longer.

* * * * *